United States Patent
Reynolds et al.

(10) Patent No.: US 8,022,331 B2
(45) Date of Patent: Sep. 20, 2011

(54) METHOD OF MAKING ELONGATED MEDICAL DEVICES

(75) Inventors: Brian R. Reynolds, Ramsey, MN (US); Peter Skujins, Minneapolis, MN (US); Dave Johnson, Hopkins, MN (US); Alan D. Eskuri, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1254 days.

(21) Appl. No.: 11/623,255

(22) Filed: Jan. 15, 2007

(65) Prior Publication Data

US 2007/0114211 A1 May 24, 2007

Related U.S. Application Data

(63) Continuation of application No. 10/375,207, filed on Feb. 26, 2003, now Pat. No. 7,169,118.

(51) Int. Cl.
*B23K 26/20* (2006.01)
*B23K 10/02* (2006.01)

(52) U.S. Cl. ................. 219/121.64; 219/121.46

(58) Field of Classification Search ............ 600/434, 600/585, 528; 219/121.64, 121.46, 121.14, 219/56; 140/112; 228/131, 173.5
See application file for complete search history.

(56) References Cited

U.S. PATENT DOCUMENTS

| | | | |
|---|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |

(Continued)

FOREIGN PATENT DOCUMENTS

AU 723040 12/1997

(Continued)

OTHER PUBLICATIONS

"Mechanical Design and Systems Handbook", H.A. Rothbart, p. 33-13 (one sheet), Dec. 1964.

*Primary Examiner* — Geoffrey S Evans
(74) *Attorney, Agent, or Firm* — Seager, Tufte & Wickhem, LLC

(57) ABSTRACT

Elongate medical devices such as guidewires can be formed from a core wire and a preformed distal cap that is configured to fit over a distal end of the core wire. The distal cap can be attached using a variety of techniques. In particular, the distal cap can be attached to the core wire using laser welding.

18 Claims, 7 Drawing Sheets

U.S. PATENT DOCUMENTS

| | | |
|---|---|---|
| 3,686,990 A | 8/1972 | Margolien |
| 3,824,368 A * | 7/1974 | Locke ...................... 219/121.64 |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,682,607 A | 7/1987 | Vaillancourt et al. |
| 4,719,924 A | 1/1988 | Crittenden et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa et al. |
| 4,832,047 A * | 5/1989 | Sepetka et al. ................. 600/585 |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,253,653 A | 10/1993 | Daigle et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,358,493 A | 10/1994 | Schweich et al. |
| 5,365,942 A | 11/1994 | Shank |
| 5,365,943 A | 11/1994 | Jansen |
| 5,368,564 A | 11/1994 | Savage |
| 5,372,144 A | 12/1994 | Mortier et al. |
| 5,376,084 A | 12/1994 | Bacich et al. |
| 5,406,960 A | 4/1995 | Corso, Jr. |
| 5,409,015 A | 4/1995 | Palermo |
| 5,411,476 A | 5/1995 | Abrams et al. |
| 5,429,139 A * | 7/1995 | Sauter ........................... 600/585 |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,465,732 A | 11/1995 | Abele |
| 5,470,330 A | 11/1995 | Goldenberg et al. |
| 5,476,701 A | 12/1995 | Berger |
| 5,477,856 A | 12/1995 | Lundquist |
| 5,488,959 A * | 2/1996 | Ales ............................. 600/585 |
| 5,496,294 A | 3/1996 | Hergenrother et al. |
| 5,497,785 A | 3/1996 | Viera |
| 5,501,228 A | 3/1996 | Lafontaine et al. |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |

| | | |
|---|---|---|
| 5,656,011 A | 8/1997 | Uihlein et al. |
| 5,658,264 A | 8/1997 | Samson |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,796 A | 6/1998 | Palermo et al. |
| 5,769,830 A | 6/1998 | Parker |
| 5,772,609 A | 6/1998 | Nguyen et al. |
| 5,782,809 A | 7/1998 | Umeno et al. |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,807,279 A | 9/1998 | Viera |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,865,768 A * | 2/1999 | Orr .................. 600/585 |
| 5,876,783 A | 3/1999 | Dobson |
| 5,891,055 A * | 4/1999 | Sauter ............... 600/585 |
| 5,897,537 A | 4/1999 | Berg et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A * | 6/1999 | Schwager ............ 600/585 |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,957,903 A | 9/1999 | Mirzaee et al. |
| 5,971,975 A | 10/1999 | Mills et al. |
| 5,984,878 A | 11/1999 | Engelson |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,045,547 A | 4/2000 | Ren et al. |
| 6,048,339 A | 4/2000 | Zirps et al. |
| 6,056,702 A * | 5/2000 | Lorenzo ............... 600/585 |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,068,623 A * | 5/2000 | Zadno-Azizi et al. ........ 600/585 |
| 6,106,485 A | 8/2000 | McMahon |
| 6,106,488 A | 8/2000 | Fleming et al. |
| 6,132,388 A | 10/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,203,485 B1 | 3/2001 | Urick |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,306,105 B1 | 10/2001 | Rooney et al. |
| 6,325,790 B1 | 12/2001 | Trotta |
| 6,336,906 B1 * | 1/2002 | Hammarstrom et al. ..... 600/585 |
| 6,338,725 B1 | 1/2002 | Hermann et al. |
| 6,346,091 B1 | 2/2002 | Jacobsen et al. |
| 6,348,041 B1 | 2/2002 | Klint |
| 6,352,515 B1 * | 3/2002 | Anderson et al. ............ 600/585 |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,494,907 B1 | 12/2002 | Bulver |
| 6,500,130 B2 | 12/2002 | Kinsella et al. |
| 6,506,205 B2 | 1/2003 | Goldberg et al. |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,579,246 B2 | 6/2003 | Jacobsen et al. |
| 6,602,207 B1 | 8/2003 | Mam et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,682,493 B2 | 1/2004 | Mirigian |
| 6,712,826 B2 | 3/2004 | Lui |
| 6,730,095 B2 | 5/2004 | Olson, Jr. et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,074,197 B2 | 7/2006 | Reynolds et al. |
| 2002/0007146 A1 * | 1/2002 | Omaleki et al. ......... 604/103.09 |
| 2002/0019599 A1 * | 2/2002 | Rooney et al. ................ 600/585 |
| 2003/0009208 A1 | 1/2003 | Snyder et al. |
| 2003/0060732 A1 | 3/2003 | Jacobsen et al. |
| 2003/0069522 A1 | 4/2003 | Jacobsen et al. |
| 2003/0125642 A1 * | 7/2003 | Kato et al. .................. 600/585 |
| 2004/0167437 A1 | 8/2004 | Sharrow et al. |
| 2008/0272615 A1 * | 11/2008 | McKnight et al. .......... 296/180.5 |
| 2010/0122735 A1 * | 5/2010 | Schramm et al. .......... 137/68.19 |

FOREIGN PATENT DOCUMENTS

| | | |
|---|---|---|
| AU | 733966 | 4/1998 |
| BR | PI 9712829 | 1/2000 |
| CA | 2266685 | 5/2006 |
| CN | 1230914 | 10/1999 |
| DE | 2539191 | 3/1976 |

| | | | | | | |
|---|---|---|---|---|---|---|
| DE | 285514 | 12/1990 | | JP | 7255855 | 10/1995 |
| EP | 0 045 931 | 2/1982 | | JP | 7275366 | 10/1995 |
| EP | 0 069 522 | 1/1983 | | JP | 751067 | 11/1995 |
| EP | 0 087 933 | 9/1983 | | JP | 8-229888 | 9/1996 |
| EP | 0 111 044 | 6/1984 | | JP | 8509141 | 10/1996 |
| EP | 0 181 174 | 5/1986 | | JP | 9-276413 | 10/1997 |
| EP | 0 565 065 | 6/1996 | | JP | 9-294813 A | 11/1997 |
| EP | 0 778 038 | 6/1997 | | JP | 10-118193 | 5/1998 |
| EP | 0 778 039 | 6/1997 | | JP | 10-305039 | 11/1998 |
| EP | 0 778 040 | 6/1997 | | JP | 10328191 | 12/1998 |
| EP | 0 812 599 | 12/1997 | | JP | 11-267224 A | 10/1999 |
| EP | 0 865 772 | 9/1998 | | JP | 2000-510722 A | 8/2000 |
| EP | 0 865 773 | 9/1998 | | JP | 2000-511083 A | 8/2000 |
| EP | 0 521 595 | 5/1999 | | JP | 2001-500808 A | 1/2001 |
| EP | 0 917 885 | 5/1999 | | JP | 2002-529137 A | 9/2002 |
| EP | 0 937 481 | 8/1999 | | JP | 2002-542901 A | 12/2002 |
| EP | 0 790 066 | 4/2000 | | JP | 2002-543896 A | 12/2002 |
| EP | 1142604 A1 * | 10/2001 | | JP | 2003-517893 A | 6/2003 |
| EP | 0 608 853 | 4/2003 | | JP | 3649604 | 2/2005 |
| EP | 0 935 947 | 12/2004 | | JP | 2005-534407 | 11/2005 |
| EP | 0 934 141 | 11/2005 | | SU | 712908 | 1/1980 |
| GB | 2214354 | 8/1989 | | SU | 758421 | 8/1980 |
| GB | 2257269 | 1/1993 | | SU | 1529365 | 12/1989 |
| JP | 58-8522 | 1/1983 | | WO | WO 90/02520 | 3/1990 |
| JP | 60091858 | 5/1985 | | WO | WO 91/13364 | 9/1991 |
| JP | 61022752 | 1/1986 | | WO | WO 92/04072 | 3/1992 |
| JP | 62023361 | 1/1987 | | WO | WO 92/07619 | 5/1992 |
| JP | 62089470 | 4/1987 | | WO | WO 93/04722 | 3/1993 |
| JP | 62299277 | 12/1987 | | WO | WO 93/11313 | 6/1993 |
| JP | 6393516 | 4/1988 | | WO | WO 95/24236 | 9/1995 |
| JP | 63-181774 | 7/1988 | | WO | WO 96/19255 | 6/1996 |
| JP | 63217966 | 9/1988 | | WO | WO 97/10022 | 3/1997 |
| JP | 1089956 | 4/1989 | | WO | WO 97/25914 | 7/1997 |
| JP | 1135363 | 5/1989 | | WO | WO 97/43949 | 11/1997 |
| JP | 1158936 | 6/1989 | | WO | WO 97/44083 | 11/1997 |
| JP | 3081831 | 4/1991 | | WO | WO 97/44086 | 11/1997 |
| JP | 03-122850 | 12/1991 | | WO | WO 98/10694 | 3/1998 |
| JP | 4061840 | 2/1992 | | WO | WO 99/11313 | 3/1999 |
| JP | 4099963 | 3/1992 | | WO | WO 00/27303 | 5/2000 |
| JP | 4213069 | 8/1992 | | WO | WO 00/30710 | 6/2000 |
| JP | 4213070 | 8/1992 | | WO | WO 00/48645 | 8/2000 |
| JP | 4236965 | 8/1992 | | WO | WO 00/57943 | 10/2000 |
| JP | 5149969 | 6/1993 | | WO | WO 00/66199 | 11/2000 |
| JP | 5-506806 | 10/1993 | | WO | WO 00/67845 | 11/2000 |
| JP | 5-309159 | 11/1993 | | WO | WO 00/72907 | 12/2000 |
| JP | 5-507857 | 11/1993 | | WO | WO 01/28620 | 4/2001 |
| JP | 6-501179 | 2/1994 | | WO | WO 01/45773 | 6/2001 |
| JP | 631749 | 4/1994 | | WO | WO 01/93920 | 12/2001 |
| JP | 6169996 | 6/1994 | | WO | WO 02/05886 | 1/2002 |
| JP | 6-63224 | 9/1994 | | WO | WO 02/13682 | 2/2002 |
| JP | 6312313 | 11/1994 | | WO | WO 02/062540 | 8/2002 |
| JP | 728562 | 5/1995 | | WO | WO 03/004086 | 1/2003 |
| JP | 7124164 | 5/1995 | | WO | WO 03/008148 | 1/2003 |
| JP | 7124263 | 5/1995 | | WO | WO 2004/012804 | 2/2004 |
| JP | 7505561 | 6/1995 | | | | |
| JP | 7037199 | 7/1995 | | | | |
| JP | 7185009 | 7/1995 | | | | |

* cited by examiner

METHOD OF MAKING ELONGATED MEDICAL DEVICES

RELATED APPLICATION

This application is a continuation of co-pending U.S. application Ser. No. 10/375,207, filed Feb. 26, 2003, which is incorporated herein by reference.

TECHNICAL FIELD

The invention pertains generally to elongate medical devices such as catheters, guidewires, and the like.

BACKGROUND

A wide variety of elongate medical devices such as catheters and guidewires have been developed. Such medical devices can be used to facilitate navigation and treatment within the anatomy of a patient. Because the anatomy of a patient may be very tortuous, it can be desirable to have particular performance features in an elongate medical device. A number of different structures and assemblies for elongate medical devices such as guidewires, catheters, and the like are known, each having certain advantages and disadvantages. There is an ongoing need to provide alternative structures and assemblies.

SUMMARY OF SOME EMBODIMENTS

The invention provides several alternative designs, materials and methods of manufacturing alternative medical device structures and assemblies.

Accordingly, an example embodiment of the invention can be found in an elongate medical device that includes an elongate shaft and a distal cap that is formed independently of the elongate shaft. A proximal end of the distal cap includes an aperture that can be configured to fit over a distal end of the elongate shaft. After the distal cap has been formed, it can be secured to the distal end of the elongate shaft.

Another example embodiment of the invention can be found in a guidewire that can be produced by providing a core wire and a distal cap. A proximal end of the distal cap can include an aperture that is configured to fit over a distal end of the core wire. The distal cap can be positioned over the distal end of the core wire by inserting the distal end of the core wire into the aperture, and then the distal cap can be attached to the distal end of the core wire.

Another example embodiment of the invention can be found in a guidewire that has a core wire and an independently formed distal cap. A proximal end of the distal cap can include an aperture that can be configured to accept the end of the core wire, and the distal cap can subsequently be attached to the distal end of the core wire.

Another example embodiment of the invention can be found in a method of producing a guidewire. A core wire can be provided, along with a distal cap. A proximal end of the distal cap can include an aperture that is configured to fit over a distal end of the core wire. The distal end of the core wire can be inserted into the distal cap aperture, and the distal cap can be attached to the distal end of the core wire.

Another example embodiment of the invention can be found in a method of producing a guidewire. A core wire can be provided, along with a tubular sleeve. The tubular sleeve can be positioned over a distal end of the core wire, and a metal ball can be positioned proximate a distal end of the tubular sleeve. At least a portion of the tubular sleeve and the metal ball can be melted via laser welding or plasma welding to form an atraumatic tip.

Another example embodiment of the invention can be found in a guidewire that includes a core wire and a distal cap. A proximal end of the distal cap can include a tubular structure that defines a lumen that is configured to fit over a distal end of the core wire. A distal end of the distal cap can define an arcuate atraumatic surface. The distal cap can be formed independently of the core wire and can be attached to the core wire by inserting the distal end of the core wire into the lumen and attaching the distal cap to the core wire.

Another example embodiment of the invention can be found in a guidewire that includes a core wire and means of providing a distal tip to the core wire, the means being formed independently and subsequently secured to a distal end of the core wire.

The above summary of some embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which.

DETAILED DESCRIPTION OF SOME EMBODIMENTS

Figure 1:
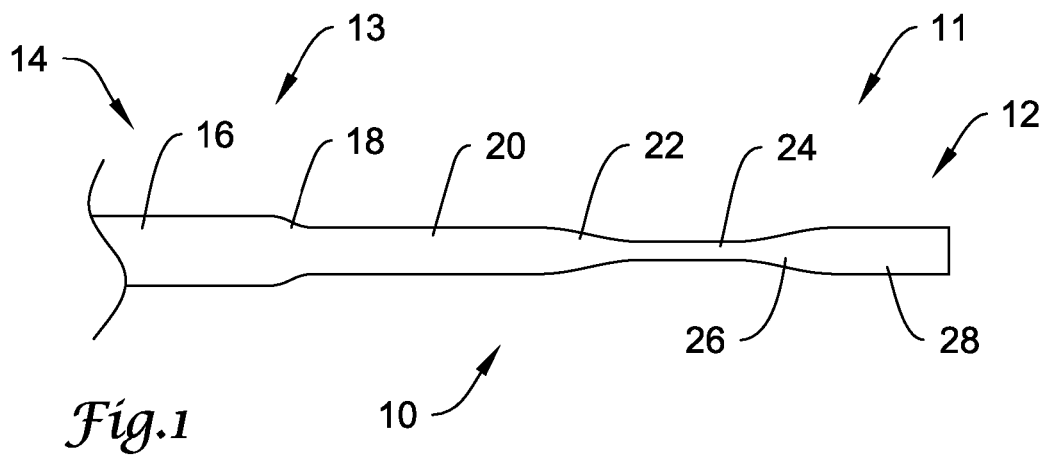
FIG. 1 is a partially sectioned side view of a distal portion of a guidewire core wire in accordance with one example embodiment of the invention, showing a profile in which a distal portion includes several tapers and a distal-most widened diameter portion.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative but non-limiting embodiments of the claimed invention.

For example, although discussed with specific reference to guidewires in the particular embodiments described herein, the invention may be applicable to a variety of medical devices that are adapted to be advanced into the anatomy of a patient through an opening or lumen. For example, the invention may be applicable to fixed wire devices, catheters (e.g. balloon, stent delivery, etc.) drive shafts for rotational devices such as atherectomy catheters and IVUS catheters, endoscopic devices, laproscopic devices, embolic protection devices, spinal or cranial navigational devices, and other such devices.

Refer now to FIGS. 1-4, which illustrate components of one example embodiment of a guidewire including a core wire 10, a distal cap 30 connected to the distal end of the core wire 10 and other structure such as a coil. FIG. 1 illustrates a distal portion of a guidewire core wire 10 that has a distal end 12 and a proximal end 14.

As shown, the core wire 10 has a proximal constant diameter section 16, an intermediate constant diameter section 20 and a distal constant diameter section 24. A proximal taper section 18 adjoins the proximal constant diameter section 16 and the intermediate constant diameter section 20. An intermediate taper section 22 adjoins the intermediate constant diameter section 20 and the distal constant diameter section 24. In some embodiments, the constant diameter section 24, or a portion thereof, can be formed into a ribbon to enhance lateral flexibility.

The core wire 10 also has a widened diameter portion 28 that is positioned at the distal end 12 of the core wire 10 and that adjoins a distal taper section 26 that is positioned between the widened diameter portion 28 and the distal constant diameter section 24. The widened diameter portion 28 can act as a heat sink in certain embodiments that use certain attachment techniques using heat to attach the distal cap 30, as discussed below, but this is not necessary.

One of skill will recognize that a guidewire core wire can have a profile different from that illustrated in FIG. 1. For example, the core wire 10 can be continuously tapered, can have a tapered section or a number or series of tapered sections of differing diameters, or can have a constant diameter. In some embodiments, the core wire 10 can be tapered or otherwise formed to have a geometry that decreases in cross sectional area toward the distal end thereof. If tapered, the core wire 10 can include a uniform or a non-uniform transition between the sections, depending on the transition characteristics desired. For example, the core wire 10 can be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

The structure used to construct the core wire 10 can be designed such that a proximal portion 13 is relatively stiff for pushability and torqueability, and a distal portion 11 is relatively flexible by comparison for better lateral trackability and steerability. For example, in some embodiments, the proximal portion 13 has a constant or generally uniform diameter along its length to enhance stiffness. However, embodiments in which the proximal portion 13 has a tapered portion or a series of tapered portions are also contemplated. The diameter of the proximal portion 13 can be sized appropriately for the desired stiffness characteristics dependent upon the material used. For example, in some embodiments, the proximal portion 13 can have a diameter in the range of about 0.010 to about 0.025 inches or greater, and in some embodiments, in the range of about 0.010 to about 0.018 inches or greater.

The distal portion 11 can likewise be constant diameter, can be continuously tapered, or can have a tapered section or a number or a series of tapered sections of differing diameters. In embodiments where the structure of core wire 10 is designed such that the distal portion 11 is relatively flexible by comparison to the proximal portion 13, the distal portion 11 can include at least one tapered or reduced diameter portion for better flexibility characteristics.

The tapered and constant diameter portions can be formed by any one of a number of different techniques, for example, by centerless grinding, stamping and the like. A centerless grinding technique can utilize an indexing system employing sensors (e.g., optical/reflective, magnetic) to avoid excessive grinding. In addition, the centerless grinding technique can utilize a CBN or diamond abrasive grinding wheel that is well shaped and dressed to avoid grabbing the core wire 10 during the grinding process. Moreover, some stamping techniques can be used to form a portion of the guidewire, for example, a distal portion, into a ribbon or other like structure.

The lengths of the proximal and distal portions 13, 11 are typically dictated by the length and flexibility characteristics desired in the final medical device. In some embodiments, the proximal portion 13 can have a length in the range of about 50 to about 300 centimeters, and the distal portion 11 can have a length in the range of about 3 to about 50 centimeters.

The core wire 10 can have a solid cross-section as shown, but in some embodiments, can have a hollow cross-section. In yet other embodiments, core wire 10 can include a combination of areas having solid cross-sections and hollow cross sections.

In some embodiments, the core wire 10 can be formed of any suitable metallic, polymeric or composite material. In some embodiments, part or all of the core wire 10 can be formed of a metal or a metal alloy. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material. The particular material used can be chosen in part based on the desired flexibility requirements of the core wire 10. In some particular embodiments, the core wire 10 can be formed from a superelastic or linear elastic nickel-titanium alloy, for example, linear elastic or superelastic (i.e. pseudoelastic) nitinol.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys, is a category designated "linear elastic" which, although is similar in chemistry to conventional shape memory and superelastic varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there is no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel-titanium alloys include those disclosed in U.S. Pat. Nos. 5,238,004 and 6,508,803, which are incorporated herein by reference. In some other embodiments, a superelastic alloy, for example a superelastic nitinol can be used to achieve desired properties.

In at least some embodiments, portions or all of the core wire 10, or other structures included within the medical device may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it may be desirable to make the core wire 10, or other portions thereof, in a manner that would impart a degree of MRI compatibility. For example, the core wire 10, or portions thereof, may be made of a material that does not substantially distort the image and create substantial artifacts (artifacts are gaps in the image). Certain ferromagnetic materials, for example, may not be suitable because they may create artifacts in an MRI image. Core wire 10, or portions thereof, may also be made from a material that the MRI machine can image. Some materials that exhibit these characteristics include, for example, tungsten, Elgiloy, MP35N, nitinol, and the like, and others.

The entire core wire 10 can be made of the same material, or in some embodiments, can include portions or sections that are made of different materials. In some embodiments, the material used to construct different portions of the core wire 10 can be chosen to impart varying flexibility and stiffness characteristics to different portions of the wire. For example, the proximal portion 13 and the distal portion 11 can be formed of different materials (i.e., materials having different moduli of elasticity) resulting in a difference in flexibility. In some embodiments, the material used to construct the proximal portion 13 can be relatively stiff for pushability and torqueability, and the material used to construct the distal portion 11 can be relatively flexible by comparison for better lateral trackability and steerability. For example, the proximal portion 13 can be formed of, for example, straightened 304v stainless steel wire, and the distal portion 11 can be formed of, for example, a straightened super elastic or linear elastic alloy (e.g., nickel-titanium) wire.

In embodiments where different portions of core wire 10 are made of different material, the different portions can be connected using any suitable connecting techniques. For example, the different portions of the core wire can be connected using welding, soldering, brazing, adhesive, or the like, or combinations thereof. Additionally, some embodiments can include one or more mechanical connectors or connector assemblies to connect the different portions of the core wire that are made of different materials. The connector can include any structure generally suitable for connecting portions of a guidewire. One example of a suitable structure includes a structure such as a hypotube or a coiled wire which has an inside diameter sized appropriately to receive and connect the different portions of the core wire. Some methods and structures that can be used to interconnect different shaft sections are disclosed in U.S. Pat. Nos. 6,918,882, and 7,074,197, which are incorporated herein by reference. Additionally, some methods and structures using expandable alloys to connect guidewire members are disclosed in U.S. Patent Publication No. 2004/0167441. Additionally, some methods and structures including alternatives structures for connecting medical device sections are disclosed in U.S. Patent Publication No. 2004/0167437, which is incorporated herein by reference.

It is to be understood that a broad variety of materials, dimensions and structures can be used to construct suitable embodiments, depending on the desired characteristics. The following examples of some dimensions are included by way of example only, and are not intended to be limiting.

In some embodiments, the core wire 10 can have the general profile set forth in FIG. 1. In some example embodiments, the proximal constant diameter section 16 can have a length that is in the range of about 10 to 120 inches and a diameter that is in the range of about 0.010 to about 0.040 inches. The intermediate constant diameter section 20 can have a length that is in the range of about 2 to about 12 inches and a diameter that is in the range of about 0.007 to about 0.025 inches. The distal constant diameter section 24 can have a length that is in the range of about 1 to about 4 inches and a diameter that is in the range of about 0.002 to about 0.004 inches. The heat sink portion 28 can have a length that is in the range of about 0.025 to about 0.25 inches and a diameter that is in the range of about 0.005 to about 0.20 inches. The proximal taper section 18, the intermediate taper section 22 and the distal taper section 26 can each have a length that is in the range of about 0.5 to about 4 inches.

Figure 2:
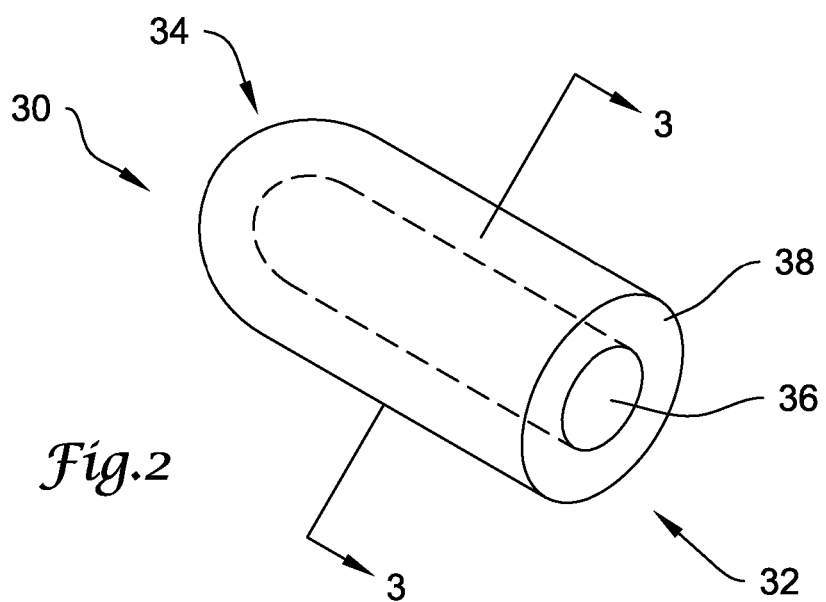
FIG. 2 is a perspective view of a distal cap in accordance with one example embodiment of the invention.
Figure 3:
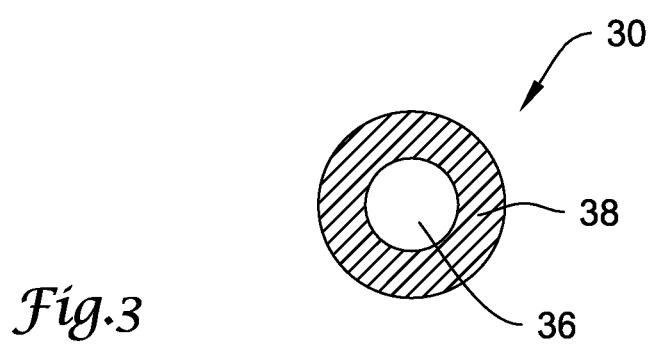
FIG. 3 is a cross-sectional view of the distal cap of FIG. 2, taken along line 3-3.

FIGS. 2 and 3 illustrate an embodiment of a distal cap 30 that is adapted and configured to fit over the distal end 12 of the core wire 10. FIG. 2 is a perspective view of the distal cap 30 while FIG. 3 is a cross-sectional view. The distal cap 30 has a proximal end 32 and a distal end 34. The distal end 34 can be configured to provide an atraumatic tip once the distal cap 30 has been secured to the core wire 10 (as discussed hereinafter). In some embodiments, as illustrated, the distal end 34 of the distal cap 30 can have a hemispherical configuration.

The proximal end 32 of the distal cap 30 can be adapted and configured to interact with the distal end 12 of the core wire 10. In some embodiments, the proximal end 32 of the distal cap 30 is configured such that the distal end 12 of the core wire 10 can fit at least partially inside the distal cap 30. In some embodiments, the proximal end 32 of the distal cap 30 can include a lumen or aperture 36 that extends at least partially into the distal cap 30 and that is surrounded by a shell 38. The shell 38 can in some embodiments have an annular or tubular form.

In some illustrative but non-limiting embodiments, the distal cap 30 can have a proximal portion that is substantially cylindrical in shape, with an outer diameter in the range of about 0.010 to about 0.040 inches and a length that is in the range of about 0.025 to about 0.250 inches. The aperture 36 can have an inner diameter that is in the range of about 0.002 to about 0.150 inches and a depth that is in the range of about 0.010 to about 0.150 inches.

The distal cap 30 can be formed from a variety of different materials, depending on desired performance characteristics. Suitable materials can include polymers, metals and metal alloys, such as those discussed with respect to the core wire 10, as well as other materials such as composites, amorphous or polycrystalline inorganics, and carbons such as pyrolitic carbon. Some illustrative but non-limiting examples of suitable metals and metal alloys include stainless steel, nickel-titanium alloys, nickel-chromium alloys, nickel-chromium-iron alloy, cobalt alloy, tungsten or tungsten alloys, Inconel 625, and other suitable materials.

In at least some embodiments, portions or all of the distal cap 30 can be doped with, made of, or otherwise include a radiopaque material, as discussed with respect to the core wire 10. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it can be desirable to make the distal cap 30 in a manner that would impart a degree of MRI compatibility, as discussed with respect to the core wire 10. Some suitable materials include, for example, tungsten, Elgiloy, MP35N, nitinol, and the like, and others.

In some embodiments, the distal cap 30 can be formed of a material such as a metallic material that is amenable, for a particular attachment method, to being welded to the distal end 12 of the core wire 10, as will be discussed in greater detail hereinafter. In some particular embodiments, it can be beneficial but not necessary for the distal cap 30 to be formed of the same metal or metal alloy as the distal end 12 of the core wire 10.

For example, if the core wire 10 is formed of stainless steel, it can be beneficial for the distal cap 30 to be formed of stainless steel or a material compatible therewith. In other embodiments, both of the distal cap 30 and the distal end 12 of the core wire 10 can be formed of the same metal alloy, such as nitinol.

A variety of different processes, such as deep drawing, roll forming or metal stamping can be used to form the distal cap 30. In some embodiments, the distal cap 30 can be metal injection molded. It is contemplated that the distal cap 30 can be formed via a casting process, with the aperture 36 formed through a drilling process. In some embodiments, the distal cap 30 can be formed using processes such as impact extrusion, cold forming or electrodeposition.

Figure 4:
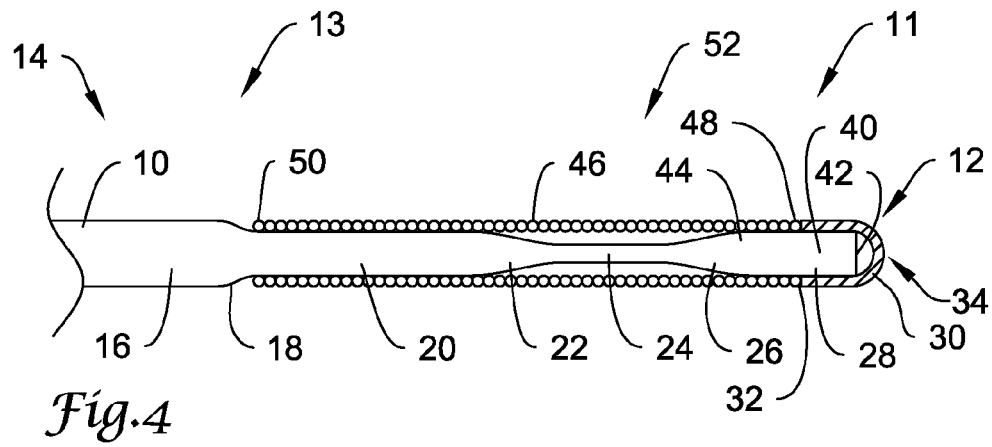
FIG. 4 is a partially sectioned side view of the guidewire core wire of FIG. 1, with the addition of a coil and the distal cap of FIG. 2.

FIG. 4 illustrates one example embodiment of a guidewire 52 including the distal cap 30 in position over the distal end 12 of the core wire 10. In some embodiments, the distal cap 30 can be positioned such that its proximal end 32 overlaps a portion of the heat sink 28. As illustrated, the distal cap 30 extends proximally such that the proximal end 32 of the distal cap 30 is positioned at a midpoint 40 that is approximately midway between the distal end 42 of the heat sink 28 and the proximal end 44 thereof. In other embodiments, the proximal end 32 can extend further proximally on the core wire 10, or may end at a more distal portion on the core wire 10.

A coil 46 having a distal end 48 and a proximal end 50 is positioned such that the distal end 48 of the coil 46 overlaps a portion of the heat sink 28. In some embodiments, the distal end 48 of the coil 46 can be positioned proximate the midpoint 40 and thus can be positioned proximate the proximal end 32 of the distal cap 30. The proximal end 50 of the coil 46 can in some embodiments be positioned proximate the proximal taper section 18. One of skill will recognize that the coil 46 can be positioned such that its proximal end 50 is proximate the intermediate taper section 22, or that a guidewire can include both a coil 46 as illustrated and one or more additional coils, for example, disposed about or under the coil 46.

The coil 46 can be formed of a variety of materials including metals, metal alloys, polymers, and the like. Some examples of material for use in the coil include stainless steel, such as 304V, 304L and 316L stainless steel, nickel-chromium alloy, nickel-chromium-iron alloy, cobalt alloy, tungsten or tungsten alloys, MP35-N, Hastelloy, Monel 400, Inconel 625, or other suitable materials.

Some additional examples of suitable material include straightened super elastic, i.e. pseudoelastic, or linear elastic alloy (e.g., nickel-titanium) wire, or alternatively, a polymer material, such as a high performance polymer. In some embodiments, the coil 46 or portions thereof can be made of or include or be coated with a radiopaque material such as gold, platinum, tungsten, or the like, or alloys thereof. In some embodiments, the coil 46 can be made of a material that is compatible with the core wire 10 and the distal cap 30.

In some embodiments, it can be advantageous for the coil 46 to include radiopaque materials, as discussed with respect to the core wire 10. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it can be desirable to make the coil 46 in a manner that would impart a degree of MRI compatibility, as discussed with respect to the core wire 10. Some suitable materials include, for example, tungsten, Elgiloy, MP35N, nitinol, and the like, and others.

The coil 46 can be formed of round or flat ribbon ranging in dimensions to achieve desired characteristics, such as flexibility. A round ribbon can be considered as having a round or oval cross-sectional shape while a flat ribbon can be considered as having a rectangular cross-sectional shape. In some embodiments, the coil 46 can be a round ribbon in the range of about 0.0005-0.004 inches in diameter, and can have a length in the range of about 0.1 to about 20 inches, however, other dimensions are contemplated.

The coil 46 can be wrapped in a helical fashion by conventional winding techniques. The pitch of adjacent turns of the coil 46 may be tightly wrapped so that each turn touches the succeeding turn or the pitch may be set such that the coil 46 is wrapped in an open fashion.

To form the guidewire assembly 52 shown in FIG. 4, the distal cap 30 and the coil 46 can be positioned proximate the core wire 10 as illustrated. The distal cap 30 and the coil 46 can be secured to the core wire 10 in any suitable manner, including for example welding, soldering, brazing, crimping, friction fitting, adhesive bonding, mechanical interlocking and the like. In these and some other example embodiments, securing the distal cap 30 to the core wire 10 may include the use of a connector and/or an expandable alloy, for example a bismuth alloy. Some examples of methods, techniques, and structures that can be used to interconnect different portions of a guidewire are disclosed in U.S. Patent Publication No. 2004/0167441 and in U.S. Pat. Nos. 6,918,882 and 7,074,197, which are incorporated herein by reference.

In some embodiments, the coil 46 and the cap 30 are welded to the core wire 10. It is to be appreciated that various welding processes can be utilized. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment that may be suitable in some embodiments is commercially available from Unitek Miyachi of Monrovia, Calif. and Rofin-Sinar Incorporated of Plymouth, Mich. Resistance welding equipment that may be useful in some embodiments is commercially available from Palomar Products Incorporated of Carlsbad, Calif. and Polaris Electronics of Olathe, Kans. TIG welding equipment that may be useful in some embodiments is commercially available from Weldlogic Incorporated of Newbury Park, Calif. Microplasma welding equipment that may be useful in some embodiments is commercially available from Process Welding Systems Incorporated of Smyrna, Tenn.

In some embodiments, laser or plasma welding can be used to secure the distal cap 30, the coil 46 and the core wire 10 securely together. In laser welding, a light beam is used to supply the necessary heat. Laser welding can be beneficial in the processes contemplated by the invention, as the use of a laser light heat source can provide pinpoint accuracy. In some embodiments, laser diode soldering can be useful, again for pinpoint accuracy. Further, securing the distal cap 30, coil 46, and the core wire 10 together may include the use of expandable alloys (e.g., bismuth alloys) similar to what is described above.

Figure 5:
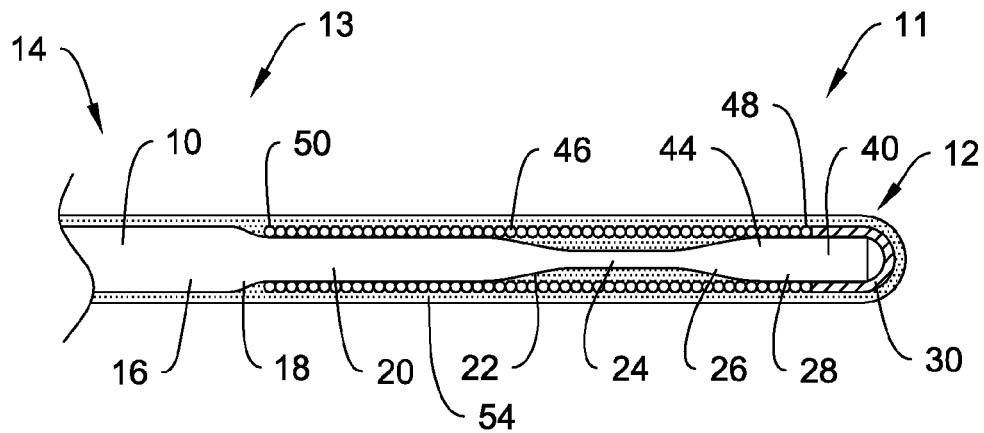
FIG. 5 is a partially sectioned side view of the guidewire construction of FIG. 4, with the addition of a polymer sleeve or sheath.
Figure 6:
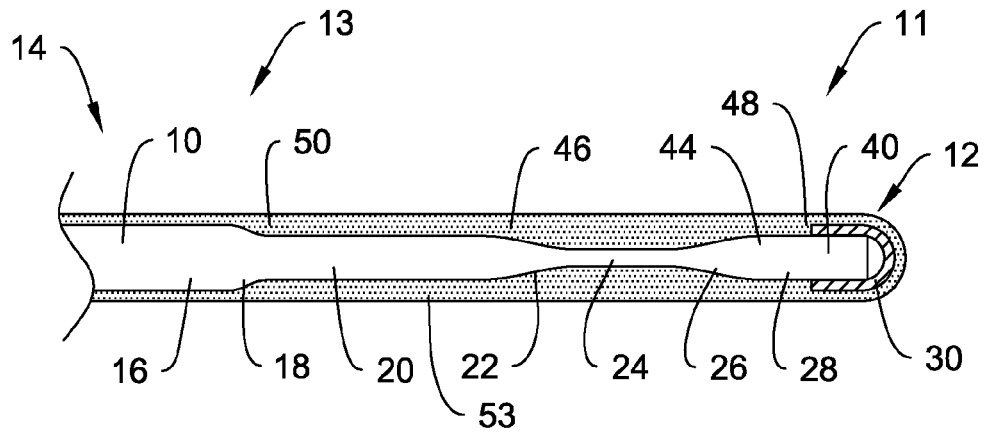
FIG. 6 is a partially sectioned side view of another example guidewire construction having a polymer sheath.

FIG. 5 shows an alternative guidewire assembly with an optional polymer sleeve 54 while FIG. 6 shows an alternative guidewire assembly having a polymer sheath 53. In this embodiment, no coil is included. Instead, a polymer tip guidewire is formed by including the polymer sheath 53 that forms a rounded tip over the distal cap 30. The polymer sheath 53 or polymer sleeve 54 can be made from any material that can provide the desired strength, flexibility or other desired characteristics. The sheath 53 or polymer sleeve 54 can in some non-limiting embodiments have a length that is in the range of about 3 to about 15 inches and can have an inner diameter that is in the range of about 0.002 to about 0.025 inches and an outer diameter that is in the range of about 0.010 to about 0.040 inches.

The use of a polymer can serve several functions, such as improving the flexibility properties of the guidewire assembly. Choice of polymers for the sleeve 53 or sheath 54 will vary the flexibility. For example, polymers with a low durometer or hardness will make a very flexible or floppy tip. Conversely, polymers with a high durometer will make a tip which is stiffer. The use of polymers for the sleeve can also provide a more atraumatic tip for the guidewire. An atraumatic tip is better suited for passing through fragile body passages. Finally, a polymer can act as a binder for radiopaque materials, as discussed in more detail below.

Some suitable materials include polymers, and like material. Examples of suitable polymer material include any of a broad variety of polymers generally known for use as guidewire polymer sleeves. In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. By employing careful selection of materials and processing techniques, thermoplastic, solvent soluble, and thermosetting variants of these materials can be employed to achieve the desired results.

Further examples of suitable polymeric materials include but are not limited to poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamid, poly(hydroxyethyl methacrylate), polyurethane, polysiloxane and their copolymers:

In some embodiments, the sheath 53, sleeve 54, or portions thereof, can include, or be doped with, radiopaque material to make the sheath 53, sleeve 54, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the sheath 53 or sleeve 54 can include a distal section having a higher level of radiopaque material loading, and a proximal section having a correspondingly lower level of loading.

In some embodiments, it is also contemplated that a separate radiopaque member or a series of radiopaque members, such as radiopaque coils, bands, tubes, or other such structures could be attached to the guidewire core wire 10, or incorporated into the core wire by plating, drawing, forging, or ion implantation techniques.

The sheath 53 or sleeve 54 can be disposed around and attached to the guidewire assembly 52 using any suitable technique for the particular material used. In some embodiments, the sheath 53 or sleeve 54 can be attached by heating a sleeve of polymer material to a temperature until it is reformed around the guidewire assembly 52. In some embodiments, the sheath 53 or the sleeve 54 can be secured to the core wire 10 using a suitable adhesive. In some other embodiments, the sheath 53 or sleeve 54 can be attached using heat shrinking techniques. In other embodiments, the sheath 53 or sleeve 54 can be co-extruded with the core wire 10. The sleeve 54 can be finished, for example, by a centerless grinding or other method, to provide the desired diameter and to provide a smooth outer surface.

A guidewire in accordance with some embodiments of the invention can optionally include a coating layer such as a lubricious coating layer over part or all of the guidewire assembly 52 or even over part or all of the polymer sheath 53 or sleeve 54. Hydrophobic coatings such as fluoropolymers provide a dry lubricity which improves guide wire handling and device exchanges. Lubricious coatings improve steerability and improve lesion crossing capability. Suitable lubricious polymers are well known in the art and may include hydrophilic polymers such as polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, the more distal portion of the guidewire is coated with a hydrophilic polymer as discussed above, and the more proximal portions is coated with a fluoropolymer, such as polytetrafluoroethylene (PTFE).

Figure 7:
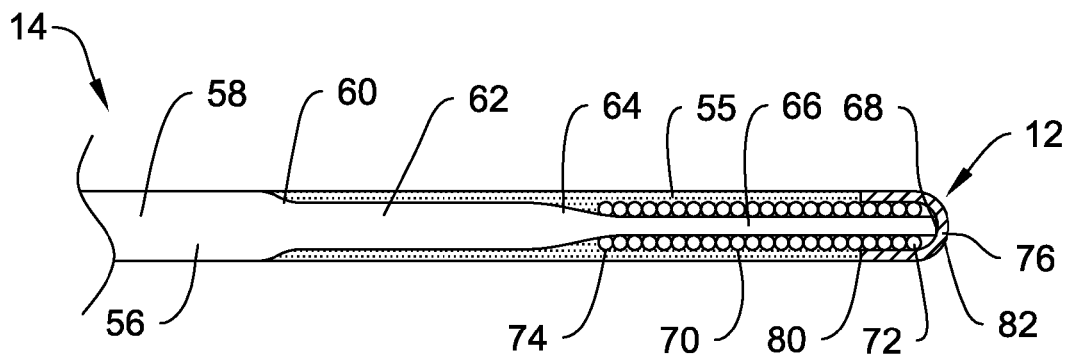
FIG. 7 is a partially sectioned side view of another example guidewire construction, showing an alternative tip configuration.
Figure 8:
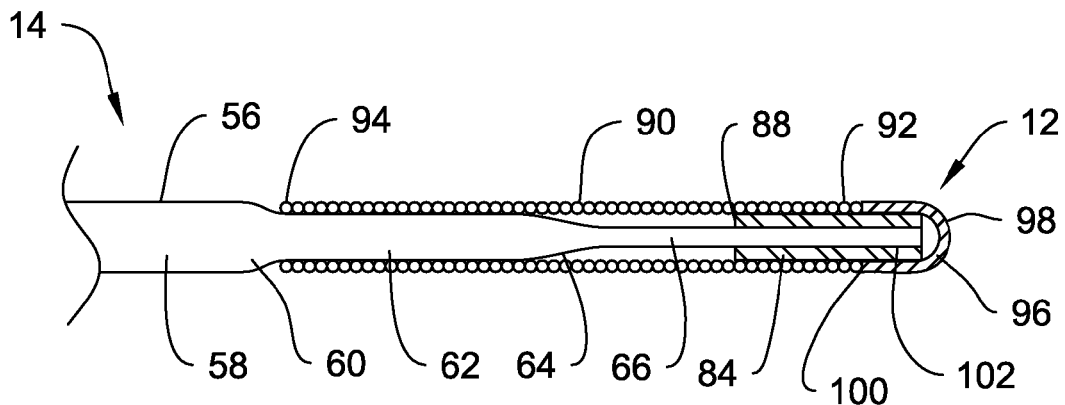
FIG. 8 is a partially sectioned side view of another example guidewire construction, showing an alternate distal cap design.
Figure 9:
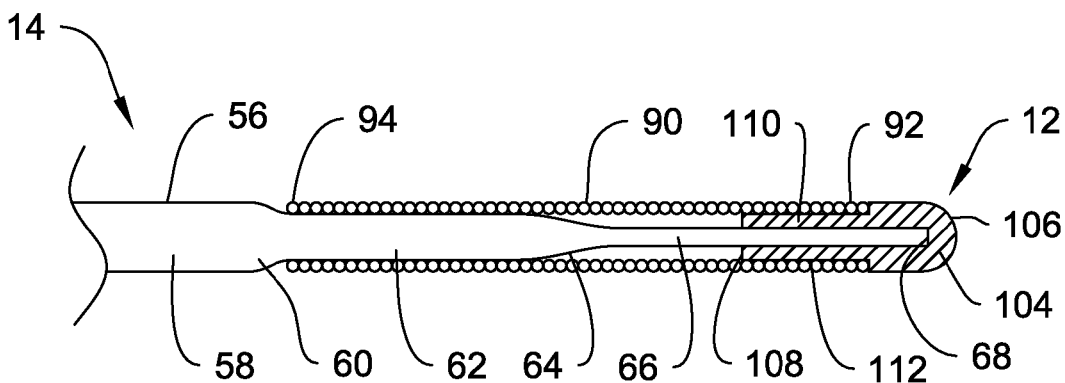
FIG. 9 is a partially sectioned side view of another example guidewire construction, showing an alternative tip configuration.

FIGS. 7 through 13 illustrate other example embodiments of the invention. FIGS. 7-9, for example, shows alternate embodiments in which a core wire 56 has, in sequence, a proximal constant diameter section 58, an adjoining proximal taper section 60, an intermediate constant diameter section 62, an adjoining distal taper section 64 and a distal constant diameter section 66. Unlike the core wire 10 of the previous Figures, the core wire 56 has no enlarged portion or heat sink at the distal end thereof. The core wire 56 can be manufactured from any suitable material, such as the metals and metal alloys discussed with respect to the core wire 10. FIGS. 7, 8 and 9 each illustrate particular embodiments of providing and securing a distal cap to the core wire 56.

In FIG. 7, a coil 70 is positioned over the distal constant diameter section 66. The coil 70 has a distal end 72 that can be positioned proximate a distal end 68 of the distal constant diameter section 66 and a proximal end 74 that can be positioned proximate the distal taper section 74. One of skill will recognize that the proximal end 74 of the coil 70 could extend further in a proximal direction, depending on the exact profile of the core wire 56. The coil 70 can be manufactured using the materials and parameters previously discussed with respect to the coil 46.

In this illustrative embodiment, a distal cap 76 having a distal end 78 and a proximal end 80 is adapted and configured to fit over the distal end 68 of the distal constant diameter section 66. In particular, the proximal end 80 of the distal cap 76 includes an aperture 82 that is sized and configured to accept the distal end 68 of the distal constant diameter section 66 as well as the distal end 72 of the coil 70. The distal cap 76 can be manufactured using similar materials and procedures as previously discussed with respect to the distal cap 30.

The distal cap 76 and the coil 70 can be secured to the core wire 56 in any suitable manner, including those described above, for example welding, soldering, brazing, crimping, friction fitting, adhesive bonding and the like. In some embodiments, laser or plasma welding can be used to secure the distal cap 76, the coil 70 and the core wire 56 securely together. Additionally, securing the distal cap 76, the coil 70, and the core wire 56 may include the use of expandable alloys (e.g., bismuth alloys) similar to what is described above.

In the embodiment shown in FIG. 7, the guidewire includes a polymeric layer 55. It is to be understood that the guidewire can include one or more additional polymeric layers as discussed previously. Moreover, such a guidewire can be partially or completely coated with a lubricious or hydrophilic coating as described hereinabove.

In FIG. 8, a distal sleeve 84 having a distal end 86 and a proximal end 88 is positioned over the distal constant diameter section 66 of the core wire 56. The distal sleeve 84 can be positioned such that the distal end 86 of the distal sleeve 84 is proximate the distal end 68 of the core wire 56. The distal sleeve 84 can be formed of any suitable material, such as the metals and metal alloys previously discussed.

As illustrated, the distal sleeve 84 can have an outer diameter that approximates an outer diameter of the intermediate constant diameter section 62. As a result, a coil 90 having a distal end 92 and a proximal end 94 can be positioned such that the distal end 92 of the coil 90 is proximate a midpoint of the distal sleeve 84 and the proximal end 94 of the coil 90 is proximate the distal taper section 60. The coil 90 can be manufactured as discussed for example with respect to the coil 46.

A distal cap 96 has a distal end 98 and a proximal end 100. In some embodiments, the distal end 98 of the distal cap 96 can form an atraumatic tip and can in particular embodiments form a hemispherical shape. In some embodiments, the proximal end 100 of the distal cap 96 can be configured to fit securely over the distal end 68 of the core wire 56 and the distal end 86 of the distal sleeve 84. In particular, the proximal end 100 of the distal cap 96 can include an aperture 102 that is sized to fit securely over the distal end 86 of the distal sleeve 84. The distal cap 96 can be manufactured as previously discussed with respect to the distal cap 30.

In the embodiment shown in FIG. 8, it is to be understood that such a guidewire can include one or more polymeric layers as discussed previously and may or may not include a coil 90 as shown. Moreover, such a guidewire can be partially or completely coated with a lubricious or hydrophilic coating as described hereinabove.

FIG. 9 shows a core wire 56 and coil 90 as described in relation to the previous Figures. A distal cap 104 has a distal end 106 and a proximal end 108. In some embodiments, the distal end 106 of the distal cap 104 can form an atraumatic tip and can in particular embodiments form a hemispherical shape. The proximal end 108 of the distal cap 104 can be configured to fit over the distal end 68 of the core wire 56. The distal cap 104 can be manufactured as previously discussed with respect to the distal cap 30.

In some embodiments, the proximal end 108 of the distal cap 104 can include an aperture 110 that is configured to accept the distal end 68 of the core wire 56. In particular, the aperture 110 can have an inner diameter that approximates an outer diameter of the core wire 56 and a depth that is sufficient to permit the distal end 68 of the core wire 56 to penetrate the distal cap 104. The proximal end 108 of the distal cap 104 can also include a shoulder 112 that can be configured to accept the distal end 92 of the coil 90.

Once the distal cap 104 has been positioned over the core wire 56 and under the coil 90, the distal cap 104 and the coil 90 can be secured to the core wire 56 in any suitable manner, including for example welding, soldering, brazing, crimping, friction fitting, adhesive bonding and the like or other technique, for example those described above in relation to method of the distal cap. In some embodiments, laser or plasma welding can be used to secure the distal cap 104, the coil 90 and the core wire 56 securely together.

In the embodiment shown in FIG. 9, it is to be understood that such a guidewire can include one or more polymeric layers as discussed previously. Additionally, in some embodiments, a coil is not used, and a polymer sheath is secured to the distal tip. Moreover, such a guidewire can be partially or completely coated with a lubricious or hydrophilic coating as described hereinabove.

FIGS. 10-13 illustrate further embodiments of the invention in which a distal tip is partially formed, is attached to a core wire and is further processed to achieve its final desired shape.

Figure 10:
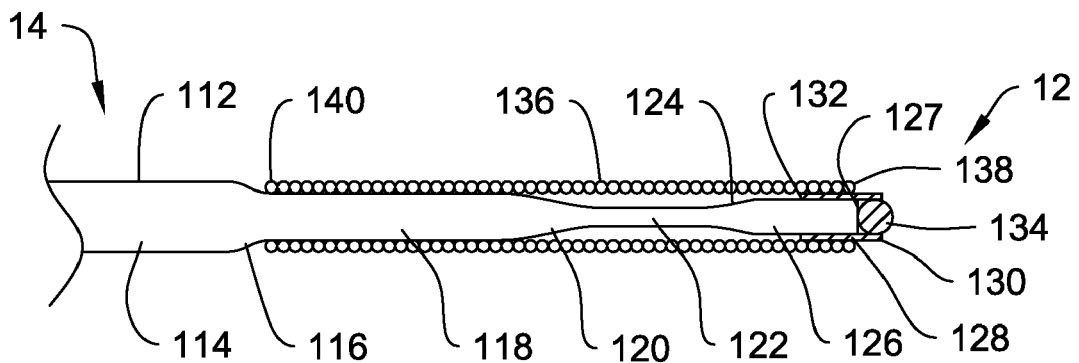
FIG. 10 is a partially sectioned side view of another example guidewire construction, showing an alternative tip configuration prior to forming the atraumatic portion.
Figure 11:
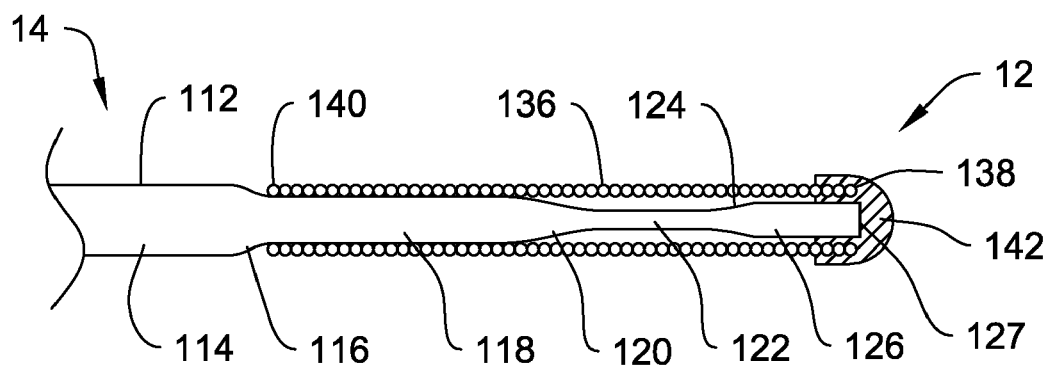
FIG. 11 is a partially sectioned side view of the guidewire construction of FIG. 10, shown after the forming of the atraumatic portion.

FIGS. 10-11 illustrate a core wire 112 that includes a proximal constant diameter section 114, a proximal taper section 116, an intermediate constant diameter section 118, an intermediate taper section 120, a distal constant diameter section 122, a distal taper section 124 and a heat sink portion 126 having a distal end 127. The core wire 112 can be manufactured from any suitable metal or metal alloy, as discussed previously.

In FIG. 10, a distal sleeve 128 having a distal end 130 and a proximal end 132 is positioned proximate the distal end 127 of the heat sink portion 126 and in some embodiments the distal end 130 of the distal sleeve 128 can extend distally beyond the distal end 127 of the heat sink portion 126. The distal sleeve 128 can be attached or connected to the core wire 112 using any suitable technique, for example, those described above. The distal sleeve 128 can be manufactured from any suitable metal or metal alloy, as discussed previously.

A metal ball 134 (see FIG. 10) can be positioned proximate the distal end 130 of the distal sleeve 128. In some embodiments the metal ball 134 can be in contact with the distal end 127 of the heat sink portion 126 while in other embodiments the metal ball 134 is held away from the heat sink portion 126 by the distal sleeve 128. The metal ball 134 can be formed of any suitable material, including metals and metal alloys. In some embodiments, it can be beneficial but not necessary for the metal ball 134 to be formed of the same material as the distal sleeve 128.

In some embodiments, the metal ball 134 can be formed from a non-fusible shape such as a sphere or ovoid that has been coated with a fusible alloy such as solder. Such a metal ball 134 can be secured by re-flowing the solder. In some embodiments, the solder could be a bismuth composition as described previously. It is contemplated that the metal ball 134 itself could be formed from a bismuth fusible alloy.

A coil 136 having a distal end 138 and a proximal end 140 can be positioned over the core wire 112 such that the distal end 138 of the coil 136 is positioned proximate the distal end 130 of the distal sleeve 128 and that the proximal end 140 of the coil 136 is positioned proximate the proximal taper section 116. The coil 136 can be manufactured in accordance with the materials and parameters discussed previously.

FIG. 11 shows an atraumatic distal cap 142 that has been formed as a result of at least partially melting the metal ball 134 and the distal sleeve 128. The metal ball 134 and the distal sleeve 128 can be at least partially melted using a variety of techniques. In some embodiments, the metal ball 134 and the distal sleeve 128 can be partially melted using a welding process, such as laser welding or plasma welding. In some embodiments (not illustrated), it is contemplated that the distal end 138 of the coil 136 and even the distal end 127 of the heat sink portion 126 may also partially melt to form a portion of the atraumatic distal cap 142.

In the embodiment shown in FIGS. 10-11, it is to be understood that such a guidewire can include one or more polymeric layers as discussed previously and does not necessarily include a coil, especially if the guidewire has a polymer tip. Moreover, such a guidewire can be partially or completely coated with a lubricious or hydrophilic coating as described hereinabove.

Figure 12:
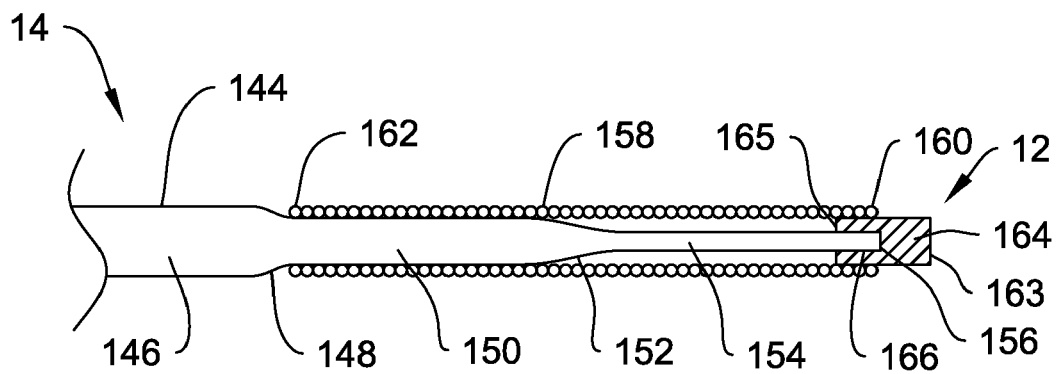
FIG. 12 is a partially sectioned side view of another example guidewire construction showing an alternative tip configuration prior to forming the atraumatic portion.
Figure 13:
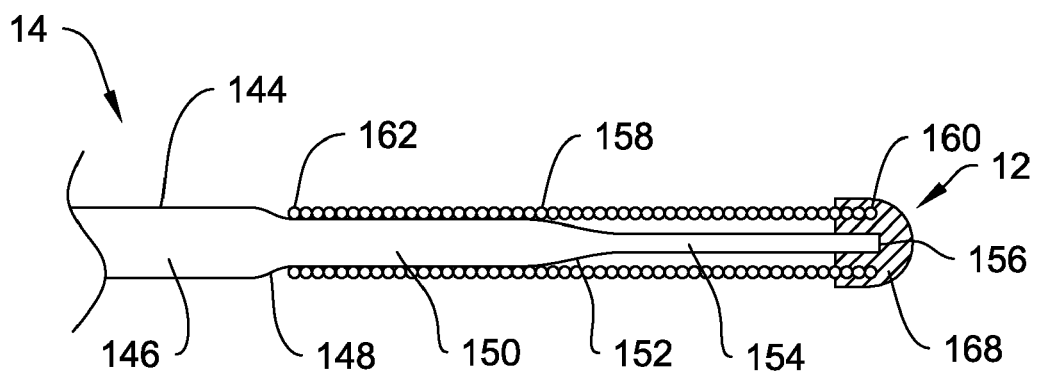
FIG. 13 is a partially sectioned side view of the guidewire construction of FIG. 12, shown after the forming of the atraumatic portion.

FIGS. 12 and 13 illustrate a core wire 144 that includes a proximal constant diameter section 146, a proximal taper section 148, an intermediate constant diameter section 150, a distal taper section 152 and a distal constant diameter section 154 having a distal end 156. The core wire 144 can be manufactured from any suitable metal or metal alloy, as discussed previously.

In FIG. 12, a preformed distal cap blank 164 has been positioned over the distal end 156 of the distal constant diameter section 154. The distal cap blank 164 can be formed of any suitable material, including the metals and metal alloys discussed with respect to other embodiments of the invention. In some embodiments, the distal cap blank 164 can include an aperture 166 that has been formed in a proximal end 165 of the distal cap blank 164. As illustrated, the distal cap blank 164 has a distal end 163 having a squared-off profile. In other embodiments, the distal cap blank 164 can be formed having a hemispherical or otherwise curved distal end 163.

A coil 158 having a distal end 160 and a proximal end 162 can be positioned over the core wire 144 such that the distal end 160 of the coil 158 is positioned proximate the distal end 163 of the distal cap blank 164 and that the proximal end 162 of the coil 158 is positioned proximate the proximal taper section 148. The coil 158 can be manufactured in accordance with the materials and parameters discussed previously.

FIG. 13 shows an atraumatic distal cap 168 that has been formed as a result of at least partially melting the distal cap blank 164. In some embodiments (not illustrated), it is contemplated that the distal end 160 of the coil 158 may also partially melt to form a portion of the atraumatic distal cap 168.

In the embodiments shown, it is to be understood that such a guidewire can include one or more polymeric layers as discussed previously. Moreover, such a guidewire can be partially or completely coated with a lubricious or hydrophilic coating as described hereinabove.

Figure 14:
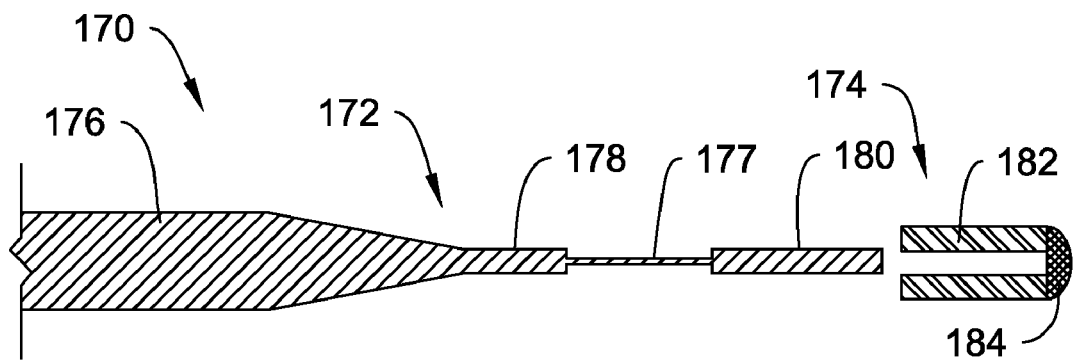
FIG. 14 is a cross-sectional exploded view of some of the components of another example medical device.

FIG. 14 is an exploded view of some of the components of another example medical device 170, which is similar to the other devices described herein. Device 170 may include a core wire 172 and a distal cap 174. Core wire 172 can be manufactured from any suitable materials including those described herein. For example, core wire 172 may include a metal (such as stainless steel, nickel-titanium alloy, etc.), polymer, metal-polymer composite, and the like. In at least some embodiments, core wire 172 may include a proximal section 176, a distal section 178, and an enlarged distal end section 180. Additionally, distal section 178 may include a ribbon 177 formed in the wire 172 or otherwise disposed between enlarged distal section 180 and distal section 178. Proximal section 176 may be similar to other proximal core wire sections described herein. For example, proximal section 176 may be configured to be sufficiently stiff to provide device 170 with the desired level of pushability and torqueability. Similarly, tapered distal section 178 may be tapered, for example, in order to increase the distal flexibility of device. Enlarged distal end section 180 may be configured to attach to distal cap 174 as described in more detail below. In some embodiments, a ribbon can be formed or otherwise disposed adjacent cap 174 and core wire 172. For example, the ribbon may be disposed behind cap 174.

Distal cap 174 may include a tubular body portion 182 and a generally atraumatic tip portion 184. In some embodiments, body portion 182 may comprise a hypodermic tube made of a suitable material. Some examples of suitable materials include stainless steel, nickel-titanium alloy, nickel-chromium alloys such inconel (including inconel 625), or any other suitable material including any of those described herein. Tip portion 184 may include a solder ball or other suitable structure that can be coupled to body portion 182. Tip portion 184 can be coupled to body portion 182 in any suitable manner. For example, tip portion 184 can be soldered, welded (including plasma, laser, and other known welding techniques), thermal bonding, chemical bonding, adhesive bonding, mechanical bonding, frictional fitting, and the like. Distal cap 174 can be formed prior to attachment to core wire 172.

Figure 15:
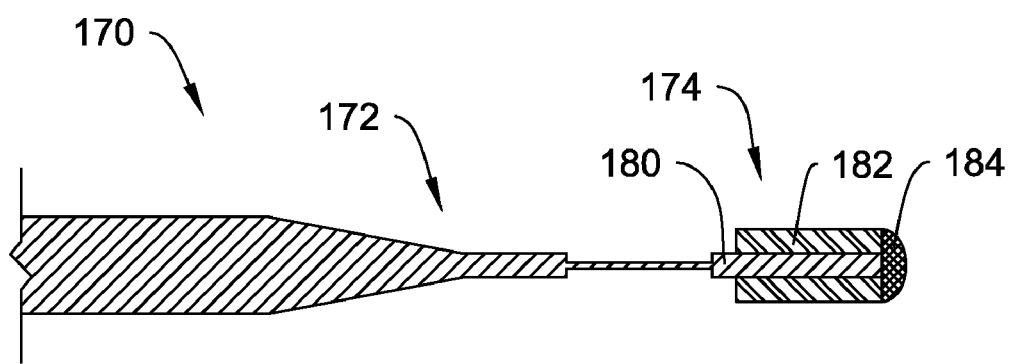
FIG. 15 is a cross-sectional side view depicting the device shown in FIG. 14 partially assembled.

Distal cap 174 may be coupled to core wire 172 as shown in FIG. 15. In at least some embodiments, body portion 182 of distal cap 174 can be disposed over enlarged distal end section 180. According this embodiment, enlarged distal end section 180 may be sized to fit within tubular body portion 182. Cap 174 can be coupled, attached, or otherwise secured to core wire 172 in essentially any known way including those listed above. For example, distal end section 180 and body portion 182 can be coupled by laser welding. In this and other embodiments that include the use of thermal energy or otherwise including heat, enlarged distal end section 180 may act as a heat sink to help absorb and distribute the heat generated by the coupling process. This may help reduce the possibility that heat could damage core wire 172.

Figure 16:
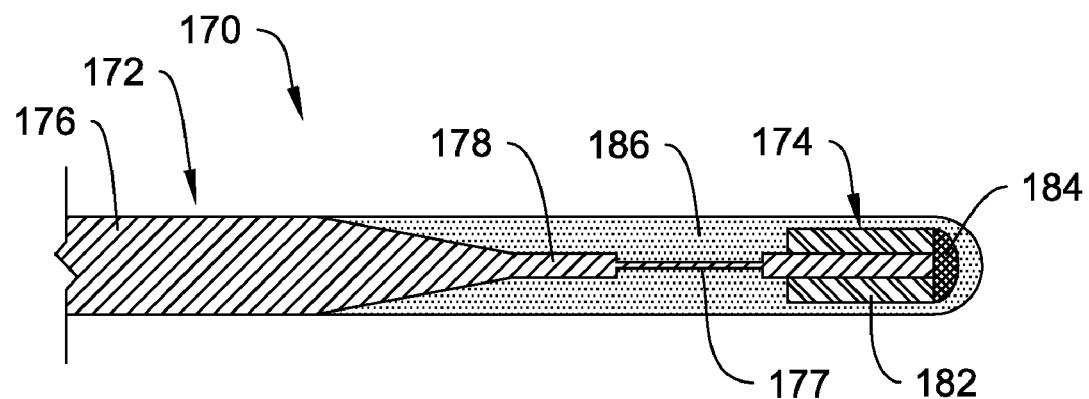
FIG. 16 is a cross-sectional side view of the example medical device of FIGS. 14 and 15 including a covering.

A covering or sheath 186 may be disposed over a portion of core wire 172 and/or cap 174 as shown in FIG. 16. Similar to what is described above, sheath 186 may be made of essentially any appropriate material including suitable polymers and the like. In some embodiments, sheath 186 may be disposed over tapered distal section 178 and extend distally to define a generally rounded tip for device 170. Additionally, sheath 178 may extend proximally toward proximal section 176.

Figure 17:
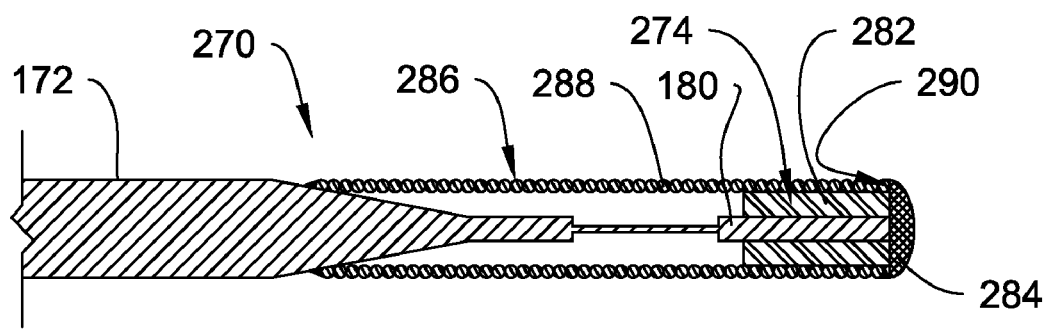
FIG. 17 is a cross-sectional side view of another example medical device.

Another example medical device 270 is illustrated in FIG. 17. Device 270 is similar to device 170, except that covering 286 may comprise a spring tip that includes a coil 286. Coil 286 may be made from suitable materials including those listed herein and may extend, for example, distally from an attachment point adjacent proximal section 176 over distal section 178. The configuration of coil 286 may vary. For example, coil 286 may have essentially any appropriate shape, thickness, length, pitch, material composition, and the like including any of the various properties and configurations described herein.

Distal cap 274 may include tip portion 284. In some embodiments, tip portion 284 may be larger than tip portion 184 (as shown in FIGS. 14-16) so that it has a width or outside diameter that is greater than body portion 282. According to this embodiment, tip portion 284 may extend laterally beyond body portion 282 and define a shoulder region 290. Attaching cap 274 to core wire 172, thus, may include configuring coil 286 so that it extends over body portion 282 and terminates adjacent should region 290. This can occur by configuring coil 286 prior to, during, or after attaching cap 274 to core wire 172. Alternatively, tip portion 284 can be attached to coil 286 and body portion 282 after coupling cap 274 to enlarged section 180.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

We claim:

1. A method of manufacturing a medical device, comprising the steps of:
    providing a core wire having a proximal section and a distal section, the distal section of the core wire formed from a metal or metal alloy, the distal section including a widened diameter portion at a distal end of the core wire;
    providing a tubular body member having a proximal portion and a distal portion, the tubular body defining a lumen therethrough having an inner diameter configured to fit over an outer diameter of the widened diameter portion;
    attaching a tip to the distal portion of the tubular member to form a distal cap member comprising the tubular body member and the tip, the distal cap member formed from a metal or metal alloy that is welding-compatible with the metal or metal alloy of the distal section of the core wire;
    after forming the distal cap member, inserting the widened diameter portion of the distal section of the core wire into the lumen of the tubular body; and
    after inserting the widened diameter portion into the lumen, welding the distal cap member to the distal section of the core wire; wherein the widened diameter portion of the distal section of the core wire is a heat sink during the welding.

2. The method of claim 1, wherein attaching a tip comprises attaching an atraumatic tip.

3. The method of claim 1, wherein attaching a tip comprises providing a solder ball.

4. The method of claim 1, wherein providing a core wire comprises providing a linear elastic core wire made of an alloy of nickel and titanium.

5. A method of producing a guidewire, comprising:
    providing a core wire having a distal end and a proximal end, the distal end including a widened diameter portion;
    providing a metallic tubular sleeve having a distal end and a proximal end;
    positioning the tubular sleeve over the widened diameter portion at the distal end of the core wire;
    positioning a metal ball proximate the distal end of the tubular sleeve; and
    melting at least a portion of the tubular sleeve and the metal ball via laser or plasma welding to form an atraumatic tip.

6. The method of claim 5, wherein the metal ball and the tubular sleeve are formed of metallic materials that are welding-compatible with the core wire.

7. The method of claim 5, further comprising positioning a coil over the distal end of the core wire prior to melting the tubular sleeve and the metal ball.

8. A method of producing a guidewire, comprising:
provides a core wire having a distal end and a proximal end, the distal end of the core wire including a widened diameter portion;
providing a distal cap having a distal end and a proximal end, the proximal end of the distal cap comprising an aperture configured to fit over the widened diameter portion at the distal end of the core wire;
inserting the distal end of the core wire into the distal cap aperture; and
welding the distal cap over the distal end of the core wire.

9. The method of claim 8, further comprising positioning a distal sleeve between the distal end of the core wire and an inner surface of the distal cap.

10. The method of claim 9, wherein the distal sleeve is secured to the distal end of the core wire and the distal cap is secured to the distal sleeve via either laser welding or plasma welding.

11. The method of claim 8, wherein the distal cap is formed via injection molding.

12. The method of claim 11, wherein securing the distal cap over the distal end of the core wire comprises melting at least part of the distal cap via laser or plasma welding.

13. The method of claim 8, further comprising positioning a coil having a distal end and a proximal end, where the distal end of the coil is positioned proximate the distal portion of the core wire.

14. The method of claim 13, wherein the distal end of the coil extends distally to a position proximal of the distal end of the core wire, and the proximal end of the distal cap extends proximally to the same position.

15. The method of claim 14, wherein the distal cap, the distal end of the coil and the distal end of the core wire are attached via welding.

16. The method of claim 15, wherein the distal cap, the coil and the core wire are all formed of welding-compatible metallic materials.

17. The method of claim 8, wherein welding the distal cap comprises laser welding or plasma welding.

18. The method of claim 8, wherein the distal cap comprises a metallic material that is welding-compatible with the core wire, also comprising a metallic material.

\* \* \* \* \*

UNITED STATES PATENT AND TRADEMARK OFFICE
CERTIFICATE OF CORRECTION

PATENT NO. : 8,022,331 B2
APPLICATION NO. : 11/623255
DATED : September 20, 2011
INVENTOR(S) : Brian R. Reynolds et al.

It is certified that error appears in the above-identified patent and that said Letters Patent is hereby corrected as shown below:

Column 13
Line 14, delete "mariner", and insert therefor -- manner --.

Signed and Sealed this
Eighth Day of November, 2011

David J. Kappos
*Director of the United States Patent and Trademark Office*